United States Patent [19]

Franke

[11] 3,952,199

[45] Apr. 20, 1976

[54] X-RAY DIAGNOSTIC INSTALLATION

[75] Inventor: Kurt Franke, Erlangen, Germany

[73] Assignee: Siemens Aktiengesellschaft, Erlangen, Germany

[22] Filed: Apr. 21, 1975

[21] Appl. No.: 570,164

[30] Foreign Application Priority Data

May 21, 1974   Germany............................ 2424634

[52] U.S. Cl................................ 250/402; 250/408; 250/413
[51] Int. Cl.².......................................... H05G 1/00
[58] Field of Search ........... 250/401, 402, 408, 409, 250/413, 416

[56] References Cited
UNITED STATES PATENTS 3,585,391   6/1971   Siedband ............................ 250/416
3,902,069   8/1975   Skarke ................................ 250/402

Primary Examiner—Craig E. Church
Attorney, Agent, or Firm—Haseltine, Lake & Waters

[57] ABSTRACT

An X-ray diagnostic installation having a patient support arrangement, an X-ray tube for transilluminating a patient, a high-voltage generator for the X-ray tube, a control installation for the high-voltage generator and for a heating filament voltage generator, a plurality of exposure systems for X-ray images which are selectively employable in conjunction with the X-ray tube, and an organ selecting arrangement for the organ-programmed setting of the exposure values for each exposure system, which possesses a switch position for each organ whose exposure volume is programmed, in which switch means for the exposure values associated with the particular switch position is actuated for the setting of the programmed exposure value. The X-ray diagnostic installation has a single organ selector which is common to all exposure systems, and that there is provided a selector arrangement by means of which the switch means associated with the one switch position of the organ selector is connectable to the setting means for the exposure values corresponding to the exposure program for the currently selected exposure system and the organ which is associated with the switch position.

5 Claims, 4 Drawing Figures

U.S. Patent  April 20, 1976  Sheet 1 of 2  3,952,199
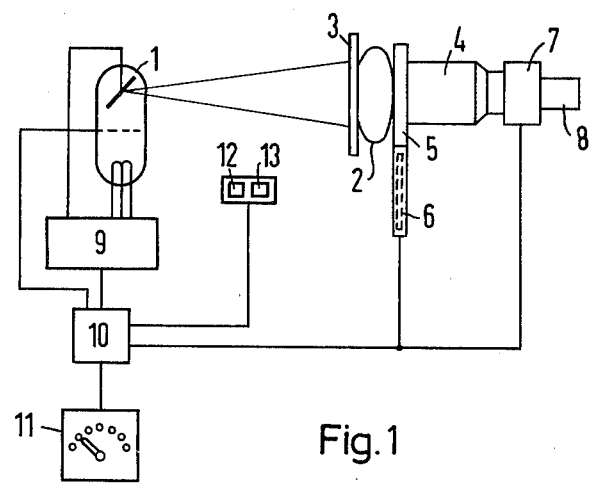
Fig.1
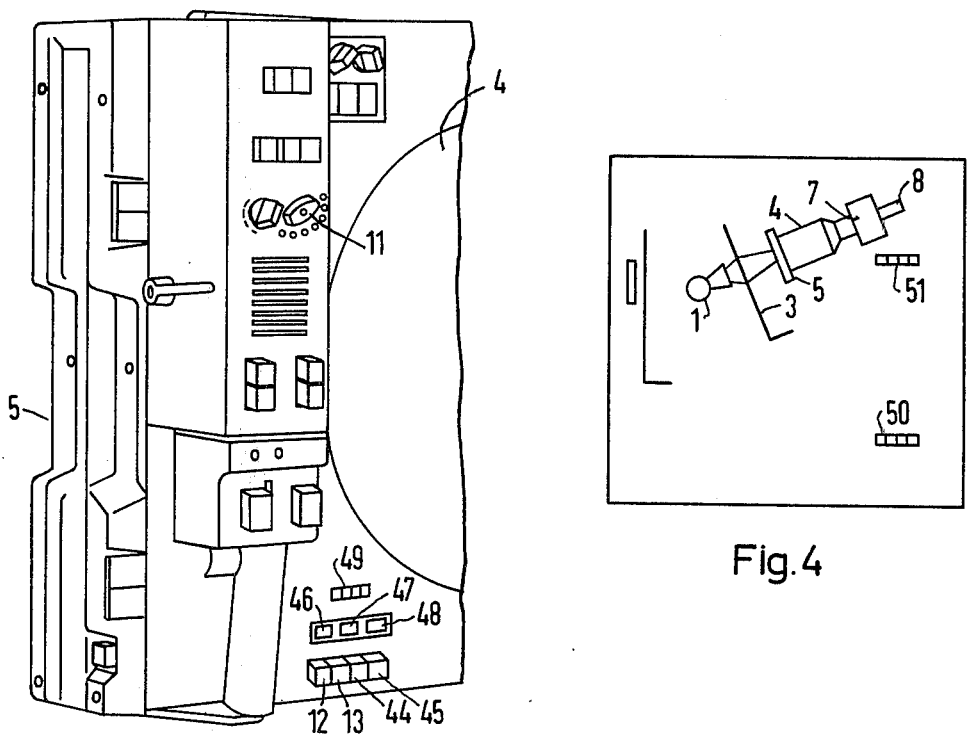
Fig.3
Fig.4

X-RAY DIAGNOSTIC INSTALLATION

FIELD OF THE INVENTION

The present invention relates to an X-ray diagnostic installation.

DISCUSSION OF THE PRIOR ART

By means of the prospectus "Tridoros Optimatic" of Siemens AG, print reference MR 50/1001, there has become known an X-ray diagnostic installation wherein a plurality of X-ray tubes is selectively actuatable at a common high-voltage and filament voltage generator, and wherein an operating panel or console is provided for each respective exposure or photographing system, at which the exposure values or magnitudes may be selected in an organ-programmed manner. In such an X-ray diagnostic installation it may occur that, with one and the same X-ray tube and two different exposure systems, for example, an X-ray targeting apparatus for direct exposures and a camera for indirect exposures, operation may be carried out from the output of an X-ray image amplifier. In the known X-ray diagnostic it is required that, for the photographing or exposure of the same organ of a patient using the same X-ray tube and different exposure systems, different organ selectors must be actuated for the setting of the exposure values. In actual practice, however, this has been found as being disruptive. The operating or manipulating is, in particular, not easily surveillable when the organ selector which is associated with an X-ray targeting apparatus is located on the X-ray targeting apparatus itself, and when the camera which is provided for an X-ray image amplifier located at the output of the X-ray targeting apparatus, has provided therefor a special operating or control console for the organ-programmed setting of the exposure values. In this instance, the operator of the installation must set the exposure values for direct exposures at the targeting apparatus, and for indirect exposures at the control panel or console.

SUMMARY OF THE INVENTION

Accordingly, it is an object of the present invention to provide an X-ray diagnostic installation having a patient support arrangement, an X-ray tube for transilluminating a patient, a high-voltage generator for the X-ray tube, a control installation for the high-voltage generator and for a heating filament voltage generator, a plurality of exposure systems for X-ray images which are selectively employable in conjunction with the X-ray tube, and an organ selecting arrangement for the organ-programmed setting of the exposure values for each exposure system, which possesses a switch position for each organ whose exposure volume is programmed, in which switch means for the exposure values associated with the particular switch position is actuated for the setting of the programmed exposure value, and which is considerably simplified in its construction and in operation in comparison with the current state of the art.

The foregoing object is inventively achieved in that in the X-ray diagnostic installation has a single organ selector which is common to all exposure systems, and there is provided a selector arrangement by means of which the switch means associated with the one switch position of the organ selector is connectable to the setting means for the exposure values corresponding to the exposure program for the currently selected exposure system and the organ which is associated with the switch position. In the inventive X-ray diagnostic installation, only a single organ selector is associated with an X-ray tube, even when it operates with a plurality of exposure systems, at which the exposure values are selected for each exposure system. The programming of the correct exposure values for the individual switch positions of the organ selector is hereby carried out by means of a selector switch which connects the organ selector with the setting means for the exposure data in correspondence with the selected exposure system.

A particularly advantageous construction of the object of the invention is attained when the exposure system is an X-ray targeting apparatus for direct exposures, and wherein the organ selector and the actuating elements of the selector arrangement are located directly on the targeting apparatus. In this embodiment, independently of the selected exposure system, there is always actuated an organ selector which is located on the X-ray targeting apparatus for selection of the exposure values. A further suitable construction of the invention is obtained when control lamps are located on the targeting apparatus for surveillance of the function of the exposure systems. In this embodiment, there is afforded the ability of optically monitoring the undisturbed function of the installation.

BRIEF DESCRIPTION OF THE DRAWINGS

Further advantageous constructions and details of the invention may now be ascertained from the following description of an exemplary embodiment thereof, taken in conjunction with the accompanying drawings; and in which:

FIG. 1 is a block circuit diagram of an X-ray diagnostic installation pursuant to the invention;

FIG. 3 is a perspective view of the control or command component of an X-ray targeting apparatus which is employable in conjunction with an X-ray diagnostic installation pursuant to FIG. 1; and FIG. 4 is a diagrammatic view of an arrangement for the surveillance of the X-ray diagnostic installation of FIG. 1.

DETAILED DESCRIPTION

Figure 2:
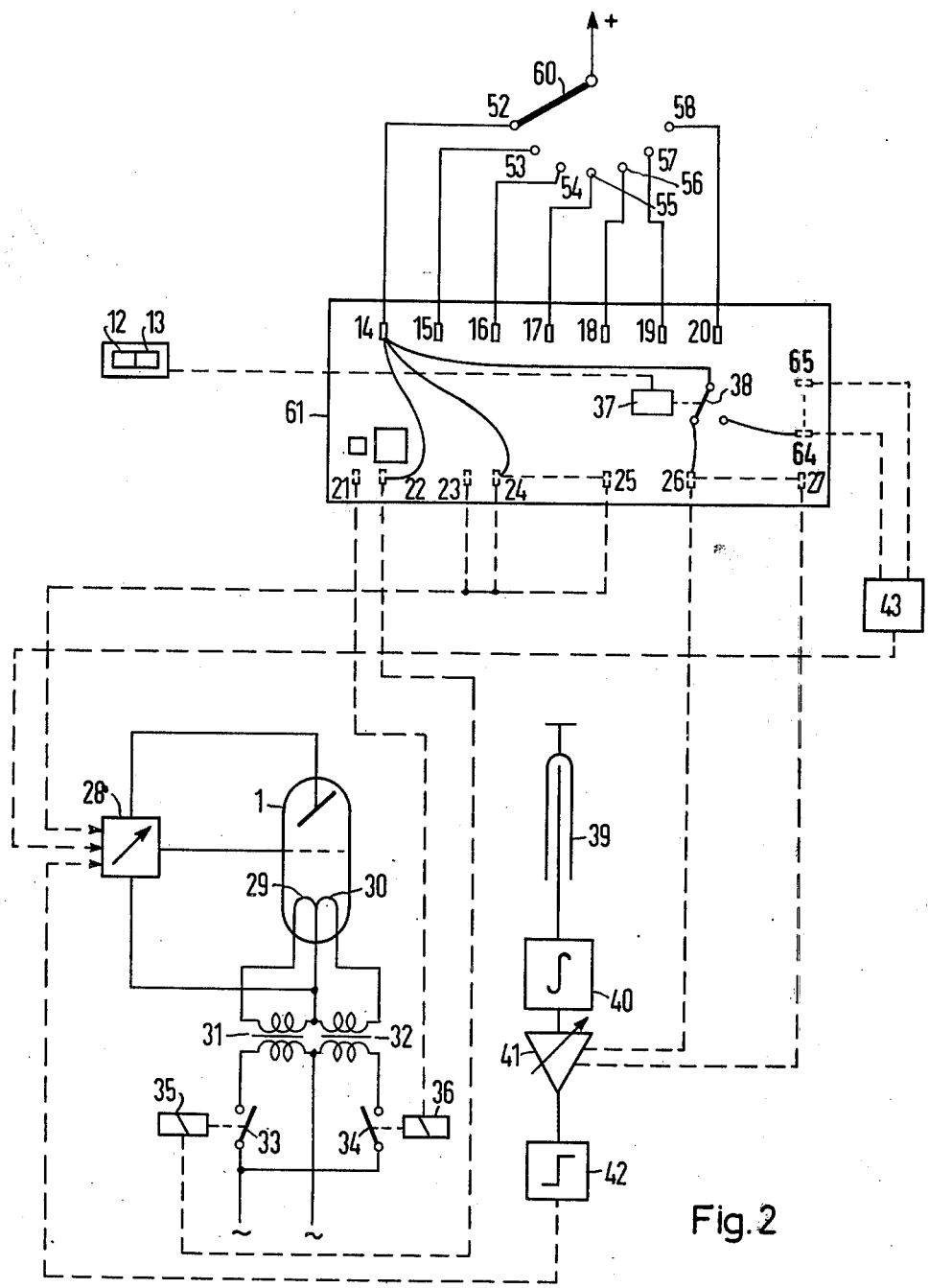
FIG. 2 is a more detailed circuit diagram for elucidating the operating manner of the X-ray diagnostic installation pursuant to FIG. 1.

Illustrated in FIG. 1 of the drawings is an X-ray tube 1 which transilluminates a patient 2 who is lying on a patient support arrangement 3. The X-ray tube 1 produces X-ray pictures on the inlet screen of an X-ray image amplifier 4 which is connected ahead of an X-ray targeting apparatus 5. The X-ray targeting apparatus 5 permits an X-ray film cassette 6 to be moved before the inlet screen of the X-ray image amplifier and, in this manner, to produce direct X-ray exposures. Connected to the output of the X-ray image amplifier 4 is a film camera 7, through the intermediary of which there may be produced indirect X-ray exposures. Furthermore, a video camera 8 is located at the output of the X-ray image amplifier 4, which controls a viewing apparatus for the optical reproduction of X-ray pictures.

The X-ray tube 1 is supplied from an X-ray generator 9 with high-voltage and with filament voltage. Connected to the X-ray generator 9 is a control element 10 which determines the exposure values, and which has an organ selector 7 associated therewith. The control element 10 is connected to the film camera 7 (for selection of the picture frequency). Furthermore, the targeting apparatus 5 is connected with the control element 10 for the initiation of the exposure from the X-ray targeting apparatus 5.

The organ selector 11 serves for the organ-programmed setting of the exposure values. It consists of a rotary step switch. Each position of the organ selector 11 has a respective organ of the patient associated therewith so that, in each position of the organ selector 111, there is automatically set the exposure value combination of the corresponding organ. Thereby, it is not necessary to actuate a number of knobs for the setting of the exposure values. The organ selector 11 is common to the X-ray targeting apparatus 5 and to the film camera 7. Serving for the selection of the time exposure system are two push-buttons 12 and 13. Upon actuation of the push-button 12 there is selected the targeting apparatus 5 and, upon actuation of the push-button 13, the film camera 7. Concurrent with the actuation of one of the push-buttons 12 and 13 there is actuated the switch means associated with the one switch position of the organ selector 11 at the setting means for the exposure data in control element 10 in correspondence with the exposure program for the presently selected exposure system and the organ which is associated with that switch postion.

The operation of the X-ray diagnostic apparatus according to FIG. 1 is extremely simple since, in the production of direct exposure as well as in the production of indirect exposures, the exposure values are set by means of one and the same organ selector.

Within the scope of the invention, the number of exposure systems which are associated with an X-ray tube are not important. When the film camera 7 is constituted of a camera for the production of individual exposures, there may additionally be connected a film camera for the production of X-ray scenes at the output of the X-ray image amplifier 4, whose exposure values are also set through the organ selector 7. In this instance there must also be provided a push-button for this film camera, in addition to the push-buttons 12 and 13. Furthermore, it is also possible, within the scope of the invention, that the X-ray tube 1 for the production of X-ray exposures be employed on a wall stand scanner when its beam path is swung away from the targeting apparatus 5, and directed onto the wall stand scanner. In this instance the selection of the exposure data may also be carried out through the organ selector 11, which has associated therewith a further push-button for the actuation of the switch means associated with the one switch position of the organ selector of the setting means for the exposure values in the control component 10, corresponding to the exposure program for the selected exposure system and the organ which is associated with that switch position.

Illustrated in FIG. 2 of the drawings is a rotary switch 60, which is a component of the organ selector and which has stationary contacts 52 through 58 associated therewith. In correspondence with the seven step positions of the organ selector 11, the rotary switch 60 possesses seven positions of which each is respectively associated with a predetermined exposure value combination for each exposure system. Conductors lead from the stationary contacts 52 through 58 of the rotary switch 60 to a distributor 61, namely, to the fixed points 14 through 20. The fixed points 14 through 20 have fixed points 21 through 27 associated therewith which permit the setting of the exposure values. The fixed point 21 serves for the selection of the small focus of the X-ray tube 1, the fixed point 22 for the selection of the large focus, the fixed points 23 through 25 for selection of the X-ray tube voltage, and the fixed points 26 and 27 for selection of the film sensitivity during the use of an automatic exposure timer. Between the fixed points 24 and 25, as well as 26 and 27, there still lie further fixed points (not shown) which are associated with intermediate values.

The X-ray tube 1 is supplied with high-voltage from a high-voltage generator 28, in which the high voltage is adjustable in a known manner. The X-ray tube 1 possesses two focuses and, consequently, two heating filaments 29 and 30 which are supplied through two heating filament transformers 31 and 32. The heating filament transformer 31 is connectable to a power supply through a relay contact 33, and the heating filament transformer 32 through a relay contact 34. The contact 33 is actuated through a relay winding 35, and the contact 34 through a relay winding 36.

A relay 37 is associated with the switches or pushbuttons 12 and 13, whose contact 37 is a switching contact which, when operation is effected with the targeting apparatus 5, meaning, when the push-button 12 is actuated, assumes the illustrated position. In this position, the contact 38 connects the fixed point 14 with the fixed point 26, so that the X-radiation can be detected by an automatic exposure timer which contains a radiation measuring chamber 39 and an integrator 40. The output voltage of the integrator 40 is then transmitted to a flip-flop 42 through an amplifier 41 which has an adjustable amplification which, in a known manner, upon reaching a predetermined ray dosage, effects the switching-off of the high voltage generator 28 and thereby of the X-ray tube 1. The automatic exposure timer is hereby adapted to be correlated to the film sensitivity, so as to vary the amplification of the amplifier 41. For this purpose there are present the fixed points 26 and 27 in the distributor 61, which are associated with predetermined amplifications of the amplifier 41.

Should operation be effected with the camera 7, then the push-button 13 is actuated and the relay 37 reverses its contact into the position illustrated in phantom lines. In this position, the automatic exposure timer 39 through 42 becomes ineffective, and the fixed point 14 is connected to a timer switch 43. The timer switch 43 is hereby conducted to the fixed point 64 and to other fixed points in the distributor 61, of which there is illustrated the fixed point 65. Each of the fixed points which lead to the timer switch 43 has a predetermined exposure time associated therewith. The X-ray tube 1 may also be grid-controlled in a manner wherein the timer switch 43 can determine the exposure period for an exposure by means of a suitable initial bias voltage. At the actuation of the push-button 13, meaning, at the selection of the camera 7 as the exposure system, there is thereby selected that particular exposure time for an individual exposure, which is associated with that particular organ which corresponds to the illustrated position of the rotary switch 60. The X-ray tube voltage and the focus hereby is the same, respectively, the same as during operation with the targeting apparatus.

Each of the fixed points 14 through 20 is connected with one of the points 21, 22 and one of the points 23 through 25, or one of the interim located points. In this manner, at each position of the rotary switch 60, during operation with the targeting apparatus 5, meaning, upon actuation of the push-button 12, there are selected the focus and the X-ray tube voltage. In this case there is also automatically set the film sensitivity. Upon actuation of the push-button 13, meaning, during operation with camera 7, there is automatically selected the focus, the X-ray tube voltage and the exposure period. Thus, for example, in the illustrated position of the rotary switch 60, for operation with the targeting apparatus 5 as well as with camera 7, there is selected since the relay 35 is excited and the contact 33 is closed, and thereby the heating filament 29 is connected to voltage. Furthermore, in the illustrated position of the rotary switch 60 an X-ray tube voltage of 40 kV is selected for both exposure systems.

Each of the fixed points 14 through 20 has a relay contact associated therewith, which corresponds to the contact 38 and which is connected with one of the fixed points 64, 65 or one of the therebetween located fixed points. All of these relay contacts, upon actuation of the push-button 13, meaning for the selection of the camera 7 as the exposure system, are so repositioned that they connect the fixed points 14 through 20 with the fixed points 64, 65 or the therebetween located fixed points, in conformance with the exposure value program. In the other positions of the rotary switch 60 there is therefore set the correct exposure time in conformance with the current organ.

Connected to the fixed points 14 through 20 may also be further setting means for the selection of further exposure values. Thus, for example, upon actuation of the push-button 13, setting means for the picture frequency of the camera 7 may be connected to the fixed points 14 through 20.

From FIG. 3 of the drawings there may be ascertained that the organ selector 11 is located on the control or command component of the X-ray targeting apparatus 5. Visible in FIG. 3 is also a part of the X-ray image amplifier 4. Four push-button are illustrated on the X-ray targeting apparatus, in effect, the push-buttons 12 and 13, and two further push-buttons 44 and 45. In accordance therewith it becomes possible to operate with the X-ray tube 1 and four exposure systems, namely, the targeting apparatus 5, which is selected through actuation of the push-button 12, the film camera 7, which is selected through the push-button 13, a film plate changer which may be brought below the patient support 3 and which is selected through the push-button 44, and a film camera for the photographing of X-ray scenes or series, which is selected through the push-button 45. Upon actuation of one of the push-buttons 12, 13, 44, 45, meaning the selection of one of the exposure systems, the individual positions of the organ selector 11 are associated with the exposure values of a completely predetermined organ for the selected exposure system so that, for all four exposure systems, the exposure values may be set by means of the organ selector 11. The interconnection of the push-buttons 12, 13, 44 and 45 with the setting means for the exposure data is carried out similarly to in FIG. 2 of the drawings. However, herein there must be provided further relays or similar circuitry elements which effect the interconnection of the setting means for the exposure data with the switch means of the organ selector (rotary switch 60 with contacts 52 through 58).

Above the row of push-buttons 12, 13, 44 and 45, are located three differently colored indicator areas 46, 47 and 48, which may be illuminated by lamps. Through these indicator areas it becomes possible to provide indication of orderly operation and interruptions during the operation, or preceding the completion of an exposure or exposure series. The indicator areas 46 through 48 thereby may be associated with different individual components of the X-ray diagnostic apparatus, and orderly operation of the corresponding individual components may be indicated through a constant or steady light, whereas interruption may be signalled through flashing lights. Thus, for example, it becomes possible to signal through a red light in area 46 the setting of the primary beam focus, through a yellow light in area 47 the occurence of X-rays afer actuation of the exposure trigger, and through a green light in area 48 the operation of camera 7. If the primary beam focus is not adjusted correctly then, after actuation of the exposure trigger, no X-radiation will be produced, or if disturbances are evident in camera 7, then the lights will flash or blink in the corresponding areas, whereas steady light will signify undisturbed operation. Located above the areas 46, 47, and 48 is a counter 49 which will permit counting of exposure completed with one of the exposure systems, for example, camera 7.

When it is desired to count the direct exposures as well as the indirect exposures, then there may be provided a surveillance arrangement with an installation viewing plan according to FIG. 4. The installation viewing plan according to FIG. 4 reproduces a picture of an exposure system which is connectable to a common high-voltage and heating filament transformer. In the illustrated example, producible by means of the X-ray tube 1, in addition to the targeting apparatus 5 and the camera 7, are also exposures with a wall-mounted scanning support. The direct exposures, in effect, the exposures with the targeting apparatus 5 or with the wall-mounted scanning support, are hereby counted through a counter 50, and the indirect exposures with the camera 7 through a counter 51.

The organ selector 11 is illustrated in FIG. 3 as being a rotary switch located on a targeting apparatus. Within the scope of the invention, in a known manner, the organ selector may also be in a known manner constituted of push-buttons associated with particular organs. The organ selector, in lieu of being located at the targeting apparatus, may also be located in a panel or console which is separated therefrom. In this case, it is, however, also essential for the present invention that for one X-ray tube and a number of exposure systems there be provided only one organ selector. Naturally, each of the switch positions of the organ selector 11 may also have a number of organs associated therewith when it is applicable to the same exposure value combination.

While there has been shown what is considered to be the preferred embodiment of the invention, it will be obvious that modifications may be made which come within the scope of the disclosure of the specification.

What is claimed is:

1. In an X-ray diagnostic installation including a patient support arrangement; an X-ray tube for transilluminating a patient; a high-voltage generator and a heating filament generator for said X-ray tube; control means for said high-voltage generator and for said heating filament generator; a plurality of exposure systems for X-ray images selectively actuatable for use with said X-ray tube; and an organ selector arrangement for the organ-programmed setting of exposure values for each exposure system, said arrangement having a switch position for each organ whose exposure values are programmed, said arrangement including switch means for the exposure values associated with the switch position for effecting the setting of the programmed exposure values, the improvement comprising: said arrangement including a single organ selector common to all of said exposure systems; and selector means for operatively connecting said switch means associated with the one switch position of said organ selector to setting means for the exposure values dependent upon the exposure program for the currently selected exposure system and the organ associated with said switch position.

2. An X-ray diagnostic installation as claimed in claim 1, one said exposure system comprising an X-ray targeting apparatus for direct exposures, said selector arrangement having actuating means, said actuating means and said organ selector being located on said targeting apparatus.

3. An X-ray diagnostic installation as claimed in claim 2, comprising control lamps being located on said targeting apparatus for surveilling the function of said exposure systems.

4. An X-ray diagnostic installation as claimed in claim 2, comprising exposure counter means being located on said targeting apparatus.

5. An X-ray diagnostic installation as claimed in claim 1, comprising surveillance means having an installation viewing plan for representing an image indicative of the exposure systems connectable to a common high-voltage and heating filament transformer; and separate counter means being connected thereto for respectively counting direct and indirect exposures.

* * * * *